United States Patent
Yoshida

(10) Patent No.: US 9,820,925 B2
(45) Date of Patent: *Nov. 21, 2017

(54) SKIN COSMETIC

(71) Applicant: KAO CORPORATION, Tokyo (JP)

(72) Inventor: Tomokazu Yoshida, Suginami-ku (JP)

(73) Assignee: KAO CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/027,568

(22) PCT Filed: Apr. 10, 2015

(86) PCT No.: PCT/JP2015/061218
§ 371 (c)(1),
(2) Date: Apr. 6, 2016

(87) PCT Pub. No.: WO2015/182259
PCT Pub. Date: Dec. 3, 2015

(65) Prior Publication Data
US 2016/0235640 A1    Aug. 18, 2016

(30) Foreign Application Priority Data

May 30, 2014 (JP) .................... 2014-113234

(51) Int. Cl.
*A61K 8/36* (2006.01)
*A61K 8/37* (2006.01)
*A61K 8/43* (2006.01)
*A61K 8/41* (2006.01)
*A61Q 19/00* (2006.01)
*A61K 8/19* (2006.01)
*A61K 8/34* (2006.01)

(52) U.S. Cl.
CPC ............... *A61K 8/43* (2013.01); *A61K 8/19* (2013.01); *A61K 8/342* (2013.01); *A61K 8/361* (2013.01); *A61K 8/37* (2013.01); *A61K 8/41* (2013.01); *A61Q 19/00* (2013.01); *A61K 2800/591* (2013.01); *A61Q 19/007* (2013.01)

(58) Field of Classification Search
CPC ............ A61K 8/38; A61K 8/41; A61K 8/342; A61K 8/19
See application file for complete search history.

(56) References Cited

U.S. PATENT DOCUMENTS 9,433,567 B2 * 9/2016 Yoshida ............... A61K 8/0204
2015/0110840 A1 4/2015 Yoshida et al.

FOREIGN PATENT DOCUMENTS

| JP | 6-345633 | 12/1994 |
|----|----------|---------|
| JP | 7-223934 A | 8/1995 |
| JP | 2003-12486 A | 1/2003 |
| JP | 2006-290751 A | 10/2006 |
| JP | 2006-312622 A | 11/2006 |
| JP | 2007-9199 A | 1/2007 |
| WO | 2015/056807 A1 | 4/2015 |

OTHER PUBLICATIONS

G. Imokawa, et al., "Stratum Corneum Lipids Serve as a Bound-Water Modulator," The Journal of Investigative Dermatology, vol. 96, No. 6, Jun. 1991, 8 pages.

T. Kaneko, et al., "Preparation and Characteristics of Arginine Oleate Liquid Crystal Holding a Large Amount of Water," Journal of Oleo Science, vol. 54, No. 6, 2005, 9 pages.

International Search Report dated Jul. 14, 2015 in PCT/JP2015/061218 Filed Apr. 10, 2015.

* cited by examiner

*Primary Examiner* — Gina Yu Justice
(74) *Attorney, Agent, or Firm* — Oblon, McClelland, Maier & Neustadt, L.L.P.

(57) ABSTRACT

The present invention provides a skin cosmetic containing the following components (A), (B), (C), (D), (E), and (F):
(A) 0.5 to 7 mass % of a linear saturated fatty acid having 12 to 22 of carbon atom,
(B) 0.01 to 5 mass % of an organic base,
(C) 0.01 to 1 mass % of an inorganic base,
(D) 0.6 to 7 mass % of a linear saturated alcohol having 12 to 22 of carbon atom,
(E) 0.1 to 20 mass % of an oil agent, and
(F) water, wherein
the total amount of the components (A) and (D) is (A)+(D)=from 1 to 14 mass %, the mass ratio of the component (A) to the total amount of the components (A) and (D) [(A)+(D)] is (A)/[(A)+(D)]=from 0.1 to 0.9, the molar ratio of the component (B) to the total amount of the components (B) and (C) [(B)+(C)] is (B)/[(B)+(C)]=from 5 to 50 mol %, and the molar ratio of the total amount of the components (B) and (C) [(B)+(C)] to the component (A) is [(B)+(C)]/(A)=more than 80 mol % and 120 mol % or less.

9 Claims, No Drawings

SKIN COSMETIC

TECHNICAL FIELD

The present invention relates to a skin cosmetic.

BACKGROUND ART

Cosmetics supplemented with moisturizers such as polyols (e.g., glycerin), various oil agents, amino acids, and hyaluronic acid have been developed for the purpose of protecting the skin from external environments such as dryness or physical stimulation or moisturizing the skin, thereby softening the skin and keeping the youthful appearance of the skin. These cosmetics protect the skin from external stimulation and also prevent water evaporation from the inside of the skin through the application of an emulsified layer containing an oil and water onto the skin, while contributing to improvement in rough skin or dry skin by imparting a given amount of moisture to the skin.

In contrast, cosmetics containing horny layer intercellular lipid components such as ceramides and further having a lamellar structure similar to intercellular lipids have been proposed (Non Patent Literature 1 and Patent Literature 1).

Meanwhile, a technique using fatty acid arginine salt is known as a technique of forming a lamellar structure without the use of ceramides, etc. (Non Patent Literature 2).

Further studies have been made on cosmetics containing fatty acid arginine salt combined with a higher alcohol or a surfactant (e.g., Patent Literature 2).
(Non Patent Literature 1) The journal of investigative dermatology, vol. 96 (6), 845-851 (1991)
(Non Patent Literature 2) J. Oleo. Sci., vol. 54 (6), 325-333 (2005)
(Patent Literature 1) JP-A-H6-345633
(Patent Literature 2) JP-A-2007-9199

SUMMARY OF INVENTION

The present invention relates to a skin cosmetic containing the following components (A), (B), (C), (D), (E), and (F)
(A) 0.5 to 7 mass % of a linear saturated fatty acid having 12 to 22 of carbon atom of carbon atom,
(B) 0.01 to 5 mass % of an organic base,
(C) 0.01 to 1 mass % of an inorganic base,
(D) 0.6 to 7 mass % of a linear saturated alcohol having 12 to 22 of carbon atom,
(E) 0.1 to 20 mass % of an oil agent, and
(F) water, wherein
the total amount of the components (A) and (D) is (A)+(D)=from 1 to 14 mass %, the mass ratio of the component (A) to the total amount of the components (A) and (D) [(A)+(D)] is (A)/[(A)+(D)]=from 0.1 to 0.9, the molar ratio of the component (B) to the total amount of the components (B) and (C) [(B) (C)] is (B)/[(B)+(C)]=from 5 to 50 mol %, and the molar ratio of the total amount of the components (B) and (C) [(B)+(C)] to the component (A) is [(B)+(C)]/(A)=more than 80 mol % and 120 mol % or less.

DETAILED DESCRIPTION OF INVENTION

When amphipathic solid fats having a high melting point, such as ceramides, are contained in oil-in-water emulsions, the separation, gelation, or the like of the emulsions over time tends to occur and makes these solid fats difficult to contain stably. Hence, there are high limitations on production methods or formulation.

Since ceramides are easily crystallized, a method using a large amount of an emulsifier for ceramides has been proposed. The problem of such preparations, however, is poor spreadability over the skin upon application.

In addition, ceramides themselves are expensive and therefore present problems associated with versatility.

The techniques using fatty acid arginine salt without the use of ceramides as described in Non Patent Literature 2 and Patent Literature 2 are insufficient in terms of the stability of an oil agent, moisturizing properties, etc.

The present invention relates to a skin cosmetic which forms a cosmetic coating film having a lamellar structure on the surface of the skin after being applied to the skin and thereby, is excellent in the stability of an oil agent in the composition, offers a non-sticky feel without an oily feel, has high moisturizing properties, and sustains the softness and gloss of the skin.

The present inventor has found that a lamellar membrane is formed and a large amount of an oil agent can be stably retained in the lamellar membrane, by combining a particular saturated fatty acid, a saturated alcohol, an organic base, an inorganic base, an oil agent, and water at a particular ratio; thus, the obtained skin cosmetic is excellent in the stability of an oil agent in the composition, offers a non-sticky feel without an oily feel, has high moisturizing properties, and sustains the softness and gloss of the skin.

A major feature of the skin cosmetic of the present invention, which has a lamellar structure, is that in a lamella formed to surround the oil agent (hereinafter, referred to as a concentric lamella), components (mainly, a fatty acid and a higher alcohol) constituting the lamella have highly dense carbon chain packing and have a robust membrane; hence, the oil agent retained in the lamellar membrane remains on the skin without being destroyed even after application to the skin.

On the other hand, most of conventional cosmetics result in the disappearance of a concentric lamella in films after application, even if the concentric lamella is formed in the preparations. Thus, the structure and properties of such a lamella seem to contribute to the excellent effects of the present invention in terms of oil agent stability, moisture-confining properties, the sustention of the softness and gloss of the skin, a non-sticky feel with a less oily feel, etc.

In general, the presence of the lamellar structure can be confirmed by conducting small-angle X-ray diffractometry and observing repeated diffraction peaks characteristic of the lamellar structure in the obtained X-ray diffraction profile. In the present invention, the concentric lamella can be confirmed under a polarization microscope (sample thickness: 25 mm). Specifically, observed maltese cross indicates the presence of the concentric lamella.

The skin cosmetic of the present invention has a stable lamellar structure and is excellent in preservation stability, particularly, the stability of an oil agent in the composition. Because even a large amount of an oil agent, when contained therein, is covered with the lamellar membrane, the skin cosmetic of the present invention offers a non-sticky feel without an oily feel, has high moisturizing properties, and sustains the softness and gloss of the skin.

(A) Linear Saturated Fatty Acid having 12 to 22 of Carbon Atom:

The component (A) used in the present invention is a linear saturated fatty acid having 12 to 22 of carbon atom, and examples thereof include lauric acid, myristic acid, palmitic acid, stearic acid, and behenic acid. Among them, a linear saturated fatty acid having 14 to 22 of carbon atom is preferred, and a linear saturated fatty acid having 16 to 22 of carbon atom is more preferred. At least any one selected from the group consisting of palmitic acid and stearic acid is further preferred from the viewpoint of forming a stable lamellar structure in the cosmetic and from the viewpoint of forming a concentric lamella having a highly dense membrane as the lamella. Stearic acid is still further preferred from the viewpoint of the stability of the lamellar structure.

At least one or two or more selected from the group consisting of these linear saturated fatty acids having 12 to 22 of carbon atom can be used as the component (A) and can form a lamellar structure in the cosmetic by neutralization with the components (B) and (C) mentioned later. Thus, the component (A) is present as a fatty acid or a salt thereof in the cosmetic. In the present invention, the content of the component (A) is an amount in terms of the fatty acid.

The content of the component (A) in the whole composition is 0.5 mass % or more, preferably 1.5 mass % or more, more preferably 2.5 mass % or more, and is 7 mass % or less, preferably 6 mass % or less, more preferably 5 mass % or less, from the viewpoint of forming a stable lamellar structure in the cosmetic and from the viewpoint of forming a concentric lamella having a highly dense membrane as the lamella. The content of the component (A) in the whole composition is from 0.5 to 7 mass %, preferably from 1.5 to 6 mass %, more preferably from 2.5 to 5 mass %.

(B) Organic Base:

The component (B) used in the present invention is an organic base, and examples thereof include alkylamines having an alkyl group having 1 to 6 of carbon atom, alkanolamines having an alkyl group having 1 to 6 of carbon atom, and basic amino acids. The component (B) functions as a neutralizing agent for the component (A).

Specifically, examples of the alkylamines include methylamine, ethylamine, propylamine, butylamine, hexylamine, dimethylamine, and diethylamine. Examples of the alkanolamines include monoethanolamine, diethanolamine, triethanolamine, N-methyl-diethanolamine, N,N-dimethyl monoethanolamine, and aminomethyl propanol. Aminomethyl propanol is preferred. Examples of the basic amino acids include lysine, histidine, and arginine. Arginine is preferred. The arginine is preferably L-arginine.

Among them, an alkanolamine having an alkyl group having 1 to 6 of carbon atom or a basic amino acid having 1 to 6 of carbon atom is preferred, an alkanolamine having an alkyl group having 3 to 6 of carbon atom or a basic amino acid having 3 to 6 of carbon atom is more preferred, a basic amino acid is further preferred, aminomethyl propanol or arginine is still further preferred, and arginine is still further preferred, from the viewpoint of neutralizing the component (A) and forming a stable lamellar structure in the cosmetic, from the viewpoint of forming a concentric lamella having a highly dense membrane as the lamella, from the viewpoint of suppressing the deposition of crystals, and from the viewpoint of enhancing moisturizing properties. The arginine is preferably L-arginine.

At least one or two or more selected from the group consisting of these organic bases can be used as the component (B). The molar ratio of the component (B) to the component (A) is preferably 10 mol % or more, more preferably 30 mol % or more, and is preferably 80 mol % or less, more preferably 60 mol % or less, from the viewpoint of enhancing the stability of the lamellar structure in the skin cosmetic, from the viewpoint of suppressing the deposition of crystals, and from the viewpoint of enhancing moisturizing properties.

The content of the component (B) in the whole composition is 0.01 mass % or more, preferably 0.1 mass % or more, more preferably 0.2 mass % or more, and is 5 mass % or less, preferably 2.5 mass % or less, more preferably 1.8 mass % or less, from the viewpoint of enhancing the stability of the lamellar structure in the skin cosmetic and enhancing moisturizing properties. The content of the component (B) in the whole composition is from 0.01 to 5 mass %, preferably from 0.1 to 2.5 mass %, more preferably from 0.2 to 1.8 mass %.

The component (B) may form salts with the component (A) and other acids in the cosmetic. In the present invention, the content of the component (B) is an amount in terms of the organic base.

(C) Inorganic Base:

The component (C) used in the present invention is an inorganic base, and examples thereof include alkali metal hydroxides such as sodium hydroxide and potassium hydroxide. The component (C) functions as a neutralizing agent for the component (A).

Among them, sodium hydroxide or potassium hydroxide is preferred, and sodium hydroxide is more preferred, from the viewpoint of neutralizing the component (A) and forming a stable lamellar structure in the cosmetic and from the viewpoint of forming a concentric lamella having a highly dense membrane as the lamella.

At least one or two or more selected from the group consisting of these inorganic groups can be used as the component (C). The molar ratio of the component (C) to the component (A) is preferably 10 mol % or more, more preferably 30 mol % or more, and is preferably 80 mol % or less, more preferably 60 mol % or less, from the viewpoint of enhancing the stability of the lamellar structure in the skin cosmetic and enhancing moisturizing properties.

The content of the component (C) in the whole composition is 0.01 mass % or more, preferably 0.1 mass % or more, more preferably 0.2 mass % or more, and is 1 mass % or less, preferably 0.75 mass % or less, more preferably 0.6 mass % or less, from the viewpoint of enhancing the stability of the lamellar structure in the skin cosmetic and enhancing moisturizing properties. The content of the component (C) in the whole composition is from 0.01 to 1 mass, preferably from 0.1 to 0.75 mass %, more preferably from 0.2 to 0.6 mass %.

The component (C) may form salts with the component (A) and other acids in the cosmetic. In the present invention, the content of the component (C) is an amount in terms of the inorganic base.

In the present invention, the molar ratio of the component (C) to the total amount of the components (B) and (C) [(B)+(C)], (B)/[(B)+(C)], is (B)/[(B)+(C)]=from 5 to 50 mol, preferably from 10 to 40 mol %, more preferably from 15 to 30 mol %, from the viewpoint of suppressing crystallization, from the viewpoint of forming a film excellent in moisture-confining properties, and from the viewpoint of suppressing sliminess.

The molar ratio of the total amount of the components (B) and (C) [(B)+(C)] to the component (A), [(B)+(C)]/(A), represents the degree of neutralization and is [(B)+(C)]/(A)=more than 80 mol % and 120 mol % or less, preferably from 90 to 100 mol %, more preferably from 95 to 100 mol %, from the viewpoint of forming a concentric lamella having a highly dense membrane, from the viewpoint of forming a film excellent in moisture-confining properties, from the viewpoint of suppressing crystallization, and from the viewpoint of suppressing foaming.

The combination of the component (B) and the component (C) is preferably aminomethyl propanol or arginine as the component (B) and sodium hydroxide or potassium hydroxide as the component (C), more preferably arginine as the component (B) and sodium hydroxide as the component (C), from a similar viewpoint.

(D) Linear Saturated Alcohol having 12 to 22 of Carbon Atom:

The component (D) used in the present invention is a linear saturated alcohol having 12 to 22 of carbon atom, and examples thereof include lauryl alcohol, myristyl alcohol, cetyl alcohol, stearyl alcohol, and behenyl alcohol. Among them, a linear saturated alcohol having 14 to 22 of carbon atom is preferred, and a linear saturated alcohol having 16 to 22 of carbon atom is more preferred. Cetyl alcohol or stearyl alcohol is further preferred, and still further preferably, the component (D) contains cetyl alcohol and stearyl alcohol, from the viewpoint of stabilizing the lamellar structure formed by the component (A) in the cosmetic and from the viewpoint of forming a concentric lamella having a highly dense membrane as the lamella. When the component (D) contains cetyl alcohol and stearyl alcohol, these alcohols may be contained each independently or as a mixture, or cetostearyl alcohol, which is a mixture thereof, may be contained.

At least one or two or more selected from the group consisting of these linear saturated alcohols having 12 to 22 of carbon atom can be used as the component (D). The content thereof in the whole composition is 0.5 mass % or more, preferably 1.5 mass % or more, more preferably 2.5 mass % or more, and is 7 mass % or less, preferably 6 mass % or less, more preferably 5 mass % or less, from the viewpoint of stabilizing the lamellar structure in the cosmetic and from the viewpoint of forming a concentric lamella having a highly dense membrane as the lamella. The content of the component (D) in the whole composition is from 0.5 to 7 mass %, preferably from 1.5 to 6 mass %, more preferably from 2.5 to 5 mass %.

At least one or two or more selected from the group consisting of the aforementioned linear saturated alcohols having 12 to 22 of carbon atom can be used as the component (D). The content thereof in the whole composition is 0.5 mass % or more, preferably 0.6 mass % or more, more preferably 0.8 mass % or more, further preferably 1.5 mass % or more, still further preferably 2.5 mass % or more, and is 7 mass % or less, preferably 6.5 mass % or less, more preferably 6 mass % or less, further preferably 5.5 mass % or less, still further preferably 5 mass % or less, from the viewpoint of stabilizing the lamellar structure in the cosmetic and from the viewpoint of forming a concentric lamella having a highly dense membrane as the lamella. The content of the component (D) in the whole composition is from 0.5 to 7 mass %, preferably from 0.6 to 6.5 mass % or less, more preferably from 0.8 to 6 mass %, further preferably from 1.5 to 5.5 mass %, still further preferably from 2.5 to 5 mass %.

In the present invention, the total amount of the components (A) and (D), (A)+(D), in the whole composition is 1 mass % or more, preferably 3.5 mass % or more, more preferably 4.5 mass % or more, and is 14 mass % or less, preferably 12 mass % or less, more preferably 10 mass % or less, from the viewpoint of enhancing the preservation stability of the cosmetic composition. The total amount of the components (A) and (D) is (A)+(D)=from 1 to 14 mass %, preferably from 3.5 to 12 mass %, more preferably from 4.5 to 10 mass %.

The mass ratio of the component (A) to the total amount of the components (A) and (D) [(A)+(D)], (A)/[(A)+(D)], is 0.1 or more, preferably 0.2 or more, more preferably 0.3 or more, and is 0.9 or less, preferably 0.8 or less, more preferably 0.7 or less, from the viewpoint of forming a lamella in the cosmetic composition while suppressing crystallization and from the viewpoint of enhancing moisturizing properties. The mass ratio of the component (A) to the total amount of the components (A) and (D) [(A)+(D)] is (A)/[(A)+(D)]=from 0.1 to 0.9, preferably from 0.2 to 0.8, more preferably from 0.3 to 0.7.

(E) Oil Agent:

The oil agent as the component (E) used in the present invention is an oil agent other than the components (A) and (D). Examples thereof include: hydrocarbon oils such as liquid paraffin, squalane, and Vaseline; ether oils such as cetyl dimethylbutyl ether, ethylene glycol dioctyl ether, and glycerol monooleyl ether; ester oils such as octyldodecyl myristate, isopropyl palmitate, butyl stearate, di-2-ethylhexyl adipate, neopentyl glycol dicaprate, trioctanoin, and benzoic acid alkyl ester; silicone oils such as dimethylpolysiloxane, cyclic dimethylpolysiloxane, methylphenylpolysiloxane, amino-modified silicone, carboxy-modified silicone, alcohol-modified silicone, alkyl-modified silicone, polyether-modified silicone, and fluorine-modified silicone; and fluorinated oils such as perfluoroalkyl ethyl phosphoric acid, perfluoroalkyl polyoxyethylene phosphoric acid, perfluoropolyether, and polytetrafluoroethylene. Alternatively, these oil agents may be derived from plants.

Among them, a hydrocarbon oil, an ester oil, and a silicone oil are preferred from the viewpoint of sustaining the gloss of the skin. The hydrocarbon oil is preferably at least one selected from the group consisting of liquid paraffin, squalane, and Vaseline. The ester oil is preferably at least one selected from the group consisting of octyldodecyl myristate, isopropyl palmitate, butyl stearate, di-2-ethylhexyl adipate, neopentyl glycol dicaprate, trioctanoin, and benzoic acid alkyl ester. The silicone oil is preferably at least one selected from the group consisting of dimethylpolysiloxane, cyclic dimethylpolysiloxane, methylphenylpolysiloxane, amino-modified silicone, carboxy-modified silicone, alcohol-modified silicone, alkyl-modified silicone, polyether-modified silicone, and fluorine-modified silicone.

An oil agent having an SP value of from 16.0 to 21.0, more preferably an SP value of from 17.0 to 20.0, further preferably an SP value of from 18.0 to 19.0, is preferably used as the component (E) from the viewpoint of sustaining the high gloss of the skin after application. Since the SP value of the oil agent in this range is close to difference in SP value from the fatty acid as the component (A) and/or the alcohol as the component (D), the concentric lamella is stably formed and the sustention of gloss is improved. In the present invention, the SP value is determined according to the calculation expression of van Krevelen.

Examples of the oil agent having such an SP value include isopropyl palmitate (SP value: 17.0), neopentyl glycol dicaprate (SP value: 17.7), 2-ethylhexyl 4-methoxycinnamate (SP value: 19.0), polyglyceryl-2 diisostearate (SP value: 20.5), alkyl benzoate (C12-C15) (SP value: 18.0 to 18.2), triethylhexanoin (SP value: 18.1), and dimethicone (10 cs) (SP value: 17). Among them, at least any one selected from the group consisting of isopropyl palmitate (SP value: 17.0), dimethicone (10 cs) (SP value: 17), alkyl benzoate (C12-C15) (SP value: 18.0 to 18.2), and triethylhexanoin (SP value: 18.1) is preferred, and at least any one selected from the group consisting of alkyl benzoate (C12-C15) (SP value: 18.0 to 18.2) and triethylhexanoin (SP value: 18.1) is more preferred, from the viewpoint of sustaining the high gloss of the skin after application.

At least one or two or more selected from the group consisting of these oil agents can be used as the component (E).

The content of the component (E) in the whole composition is 0.1 mass % or more, preferably 0.5 mass % or more, more preferably 3 mass % or more, and is 20 mass % or less, preferably 15 mass % or less, more preferably 10 mass % or less, from the viewpoint of improving the gloss of a dried film of the cosmetic. The content of the component (E) in the whole composition is from 0.1 to 20 mass %, preferably from 0.5 to 15 mass %, more preferably from 3 to 10 mass %.

In the present invention, the mass ratio of the component (E) to the total amount of the components (A) and (D) [(A)+(D)], (E)/[(A)+(D)], is preferably 0.1 or more, more preferably 0.2 or more, further preferably 0.3 or more, and is preferably 3 or less, more preferably 2 or less, further preferably 1.5 or less, from the viewpoint of enhancing moisturizing properties and from the viewpoint of sustaining the gloss of the skin. The mass ratio of the component (E) to the total amount of the components (A) and (D) [(A)+(D)], (E)/[(A)+(D)], is preferably from 0.1 to 3, more preferably from 0.2 to 2, further preferably from 0.3 to 1.5.

(F) Water:

The component (F) used in the present invention is water and serves as a solvent for the cosmetic of the present invention. The component (F) becomes a balance of the components. The components (A) to (F) can be combined to form a stable lamellar α-gel structure in the cosmetic.

The content of the component (F) in the whole composition is preferably 50 mass % or more, more preferably 60 mass % or more, and is preferably 95 mass % or less, more preferably 90 mass % or less, from the viewpoint of forming a stable lamellar structure in the cosmetic and from the viewpoint of forming a concentric lamella having a highly dense membrane as the lamella. The content of the component (F) in the whole composition is preferably from 50 to 95 mass %, more preferably from 60 to 90 mass %.

The skin cosmetic of the present invention containing the components (A) to (F) forms a lamellar structure. This cosmetic is applied to the skin to form a cosmetic coating film on the surface of the skin as a result of water evaporation. This cosmetic coating film is a film carrying a concentric lamella having a highly dense membrane. This lamellar structure forms a film excellent in moisture-confining properties and can retain a large amount of moisture between the layers. As a result, water evaporation from the skin can be suppressed, while moisture can be imparted to the skin, thereby producing high moisturizing properties. A further feature of the skin cosmetic of the present invention is that the gloss of the skin can be sustained for a long time. Although a detailed reason therefor is unclear, this is probably because the concentric lamella retained in the cosmetic coating film retains the oil agent on the surface of the skin. A further feature of the skin cosmetic of the present invention is that the softness of the skin can be sustained for a long time by retaining the oil agent on the surface of the skin for a long time. Since no foam is generated upon application, a dense layer structure can be formed on the skin so that a film excellent in moisture-confining properties is formed. This cosmetic coating film is highly flexible and is also excellent in adhesion to the skin.

(G) Nonionic Surfactant:

In the present invention, the skin cosmetic can further contain a nonionic surfactant from the viewpoint of facilitating forming the lamellar structure as described above and improving the stability of the lamellar structure, and from the viewpoint of improving gloss and suppressing foaming.

The nonionic surfactant can also prevent the skin from becoming white due to fine foams which are generated due to the friction between the skin and fingers when the skin cosmetic of the present invention is applied to the skin by fingers. As a result, the cosmetic can be well spread over the skin when applied thereto.

Examples of the nonionic surfactant include: ethylene glycol fatty acid esters such as ethylene glycol monostearic acid ester; polyethylene glycol fatty acid esters such as polyethylene glycol (2) monostearic acid ester; polyalkylene glycol alkyl ethers such as polyethylene glycol (5) decyl pentadecyl ether; polyethylene glycol hydrogenated castor oils such as polyethylene glycol (5) hydrogenated castor oil monoisolaurate; propylene glycol fatty acid esters; monoglycerin monofatty acid esters such as glycerin monoisostearic acid ester; monoglycerin difatty acid esters such as glycerin distearic acid ester and glycerin dilauric acid ester; glycerin alkyl ethers such as glycerin monoisostearyl ether; sorbitan fatty acid esters such as sorbitan monostearic acid ester; fatty acid alkanolamides; and fatty acid dialkanolamides such as lauric acid diethanolamide.

Among these nonionic surfactants, a polyalkylene glycol alkyl ether having an alkyl group having 12 to 22 of carbon atom is preferred, and a polyalkylene glycol ether having an alkyl group having 12 to 18 of carbon atom is more preferred, from the viewpoint of suppressing fine foams upon application.

At least one or two or more selected from the group consisting of these nonionic surfactants can be used as the nonionic surfactant as the component (G). The component (G) preferably contains at least two polyalkylene glycol ethers differing in the number of carbon atom in their alkyl groups by 2 or more, more preferably contains at least two selected from the group consisting of polyethylene glycol ether of lauryl alcohol (laureth-3), polyethylene glycol ether of cetyl alcohol, and polyethylene glycol ether of stearyl alcohol, and further preferably contains these 3 polyethylene glycol ethers, from the aforementioned viewpoint as well as from the viewpoint of enhancing moisturizing properties, from the viewpoint of suppressing sliminess, and from the viewpoint of enhancing the sustention of a gloss feel. In the case of using two or more polyalkylene glycol ethers having an alkyl group having 12 to 18 of carbon atom, these polyalkylene glycol ethers may be contained each independently or as a mixture, or ceteareth-20, which is a mixture of polyethylene glycol ether of cetyl alcohol and polyethylene glycol ether of stearyl alcohol, may be contained. Still further preferably, the component (G) contains laureth-3 and ceteareth-20.

The content of the nonionic surfactant as the component (G) in the whole composition is preferably 0.1 mass % or more, more preferably 0.3 mass % or more, further preferably 0.5 mass % or more, and is preferably 2 mass % or less, more preferably 1.8 mass % or less, further preferably 1.5 mass % or less, from the viewpoint of improving moisturizing properties, from the viewpoint of suppressing sliminess, from the viewpoint of improving stability, and from the viewpoint of suppressing the foaming of the cosmetic composition upon application. The content of the component (G) in the whole composition is preferably from 0.1 to 2 mass %, more preferably from 0.3 to 1.8 mass %, further preferably from 0.5 to 1.5 mass %.

The mass ratio of the total amount of the components (A) and (D) [(A)+(D)] to the component (G), [(A)+(D)]/G, is preferably 3 or more, more preferably 4 or more, further preferably 5 or more, and is preferably 30 or less, more preferably 20 or less, and further preferably 15 or less, from the viewpoint of improving moisturizing properties, from the viewpoint of suppressing sliminess, from the viewpoint of improving stability, and from the viewpoint of suppressing the foaming of the cosmetic composition. The mass ratio of the total amount of the components (A) and (D) [(A)+(D)] to the component (G), [(A)+(D)]/G, is preferably from 3 to 30, more preferably from 4 to 20, further preferably from 5 to 15.

(H) Ionic Surfactant:

In the present invention, the skin cosmetic can further contain a nonionic surfactant, from the viewpoint of forming a concentric lamella having a highly dense membrane, from the viewpoint of improving the stability of the lamellar structure, from the viewpoint of improving moisturizing properties, from the viewpoint of reducing an oily feel, from the viewpoint of improving the sustention of gloss, and from the viewpoint of suppressing foaming.

Examples of the ionic surfactant include an anionic surfactant, a cationic surfactant, and an amphoteric surfactant.

The anionic surfactant is chosen from anionic surfactants except for the component (A), and examples thereof include: alkyl sulfuric acid esters having 12 to 22 of carbon atom or salts thereof, such as sodium lauryl sulfate and potassium lauryl sulfate; alkyl ether sulfuric acid esters having 12 to 22 of carbon atom or salts thereof, such as polyoxyethylene lauryl sulfate triethanolamine; N-acyl sarcosines having 12 to 22 of carbon atom or salts thereof, such as sodium lauroyl sarcosine; alkyl phosphates having 12 to 22 of carbon atom or salts thereof, such as sodium monostearyl phosphate; alkyl ether phosphates having 12 to 22 of carbon atom of polyoxyethylene or salts thereof, such as sodium polyoxyethylene oleyl ether phosphate and sodium polyoxyethylene stearyl ether phosphate; dialkyl sulfosuccinates having 12 to 24 of carbon atom or salts thereof, such as sodium di-2-ethylhexyl sulfosuccinate; N-alkyloyl methyltaurines having 12 to 22 of carbon atom or salts thereof, such as sodium N-stearoyl-N-methyltaurine; and N-acyl glutamates having 12 to 22 of carbon atom or salts thereof, such as sodium dilauroyl glutamate, monosodium N-lauroyl glutamate, sodium N-stearoyl-L-glutamate, arginine N-stearoyl-L-glutamate, sodium N-stearoyl glutamate, and sodium N-myristoyl-L-glutamate.

The cationic surfactant is preferably a quaternary ammonium salt, and examples thereof include: alkyl ethyl ammoniums or salts thereof, such as stearyl ethyl ammonium chloride and lauryl trimethyl ammonium chloride; dialkyl dimethyl ammonium chlorides; trialkyl methyl ammonium chlorides; and alkylamines or salts thereof.

Examples of the amphoteric surfactant include alkyldimethylamine oxide, alkyl carboxy betaine, alkyl sulfobetaine, amide amino acid salts, and alkylamidopropylbetaine.

The component (H) is preferably an anionic surfactant from the viewpoint of improving the density of the lamellar membrane. The anionic surfactant is preferably one or two or more selected from the group consisting of an alkyl ether phosphate having 12 to 22 of carbon atom of polyoxyethylene or a salt thereof, sodium N-alkyloyl methyltaurine having 12 to 22 of carbon atom, and a N-acyl glutamate having 12 to 22 of carbon atom, more preferably an alkyl ether phosphate having 12 to 22 of carbon atom of polyoxyethylene or a salt thereof.

One or more of these ionic surfactants can be used as the component (H), and one of these ionic surfactants can be used alone, or two or more thereof can be used in combination.

The content of the component (H) in the whole composition is preferably 0.01 mass % or more, more preferably 0.1 mass % or more, further preferably 0.3 mass % or more, and is preferably 2 mass % or less, more preferably 1.8 mass % or less, further preferably 1.5 mass % or less, from the viewpoint of forming a concentric lamella having a highly dense membrane, from the viewpoint of improving the stability of the lamellar structure, from the viewpoint of improving moisturizing properties, from the viewpoint of reducing an oily feel, from the viewpoint of improving the sustention of gloss, and from the viewpoint of suppressing foaming. The content of the component (H) in the whole composition is preferably from 0.01 to 2 mass %, more preferably from 0.1 to 1.8 mass %, further preferably from 0.3 to 1.5 mass %.

In the present invention, the mass ratio of the component (H) to the total amount of the components (G) and (H) [(G)+(H)], {(H)/[(G)+(H)]}, is preferably 0.01 or more, more preferably 0.1 or more, further preferably 0.2 or more, and is preferably 0.75 or less, more preferably 0.6 or less, further preferably 0.5 or less, from the viewpoint of enhancing moisturizing properties, from the viewpoint of suppressing foaming, from the viewpoint of suppressing sliminess, and from the viewpoint of sustaining the gloss of the skin. The mass ratio of the component (H) to the total amount of the components (G) and (H) [(G)+(H)], {(H)/[(G)+(H)]}, is preferably from 0.01 to 0.75, more preferably from 0.1 to 0.6, further preferably from 0.2 to 0.5.

The skin cosmetic of the present invention can further contain, appropriately, for example, a thickener, a microbicide, a moisturizer, a wetting agent, a colorant, an antiseptic, a feel-improving agent, a powder, a fragrance, an anti-inflammatory agent, a whitening agent, an antiperspirant, an ultraviolet absorber, and an antioxidant as components for use in usual cosmetics, in addition to the component (A) to the component (H).

The skin cosmetic of the present invention can further contain a solid fat other than the components (A) and (D). The content thereof is preferably 10 mass % or less, more preferably 8 mass % or less, further preferably 5 mass % or less, still further preferably 3 mass % or less, from the viewpoint of stabilizing the lamellar structure.

The skin cosmetic of the present invention can be produced, for example, by: mixing the components (B), (C), and (F) and homogeneously dissolving the mixture at from 60 to 100° C. to form an aqueous phase portion; mixing the components (A), (D), and (E) and homogeneously dissolving the mixture at from 60 to 100° C. to form an oil phase portion; and homogeneously mixing the aqueous phase portion with the oil phase portion and cooling the mixture to preferably from 5 to 30° C., more preferably from 10 to 28° C., further preferably from 15 to 26° C.

The skin cosmetic of the present invention has a pH of preferably from 5.5 to 9.5, more preferably from 6.0 to 9.0, further preferably from 6.5 to 8.5, at 25° C. from the viewpoint of forming a stable lamellar structure in the cosmetic. In the present invention, the pH is determined by directly measuring the pH of a sample at 25° C. using a pH meter (F-52, manufactured by Horiba, Ltd.).

The skin cosmetic of the present invention can be prepared as, for example, a skin lotion, an emulsion, a cream, a gel, or a serum and is particularly preferably used as a cream or a gel. The skin cosmetic of the present invention can be used as a sheet-shaped cosmetic in which a sheet-shaped base material such as woven cloth or nonwoven cloth is impregnated with the skin cosmetic of the present invention or the skin cosmetic of the present invention is applied to such a base material.

The skin cosmetic of the present invention can be applied, for use, to the skin, preferably the skin except for the scalp, more preferably any of the face, the body, limbs, and the like.

The skin cosmetic of the present invention can moisturize and also gloss the skin by application to the skin.

As for the aforementioned embodiments, the present invention further discloses the following compositions and methods for using the same and methods for producing the same.

<1> A skin cosmetic containing the following components (A), (B), (C), (D), (E), and (F):
(A) 0.5 to 7 mass % of a linear saturated fatty acid having 12 to 22 of carbon atom,
(B) 0.01 to 5 mass % of an organic base,
(C) 0.01 to 1 mass % of an inorganic base,
(D) 0.5 to 7 mass % of a linear saturated alcohol having 12 to 22 of carbon atom,
(E) 0.1 to 20 mass % of an oil agent, and
(F) water, wherein
the total amount of the components (A) and (D) is (A)+(D)=from 1 to 14 mass %, the mass ratio of the component (A) to the total amount of the components (A) and (D) [(A)+(D)] is (A)/[(A)+(D)]=from 0.1 to 0.9, the molar ratio of the component (B) to the total amount of the components (B) and (C) [(B)+(C)] is (B)/[(B)+(C)]=from 5 to 50 mol %, and the molar ratio of the total amount of the components (B) and (C) [(B)+(C)] to the component (A) is [(B)+(C)]/(A)=more than 80 mol % and 120 mol % or less.

<2> A skin cosmetic containing the following components (A), (B), (C), (D), (E), and (F):
(A) 0.5 to 7 mass % of a linear saturated fatty acid having 12 to 22 of carbon atom,
(B) 0.01 to 5 mass % of an organic base,
(C) 0.01 to 1 mass % of an inorganic base,
(D) 0.6 to 7 mass % of a linear saturated alcohol having 12 to 22 of carbon atom,
(E) 0.1 to 20 mass % of an oil agent, and
(F) water, wherein
the total amount of the components (A) and (D) is (A)+(D)=from 1 to 14 mass %, the mass ratio of the component (A) to the total amount of the components (A) and (D) [(A)+(D)] is (A)/[(A)+(D)]=from 0.1 to 0.9, the molar ratio of the component (B) to the total amount of the components (B) and (C) [(B)+(C)] is (B)/[(B)+(C)]=from 5 to 50 mol %, and the molar ratio of the total amount of the components (B) and (C) [(B)+(C)] to the component (A) is [(B)+(C)]/(A)=more than 80 mol % and 120 mol % or less.

<3> The skin cosmetic according to <1> or <2>, wherein the component (A) is preferably a linear saturated fatty acid having 14 to 22 of carbon atom, more preferably a linear saturated fatty acid having 16 to 22 of carbon atom.

<4> The skin cosmetic according to any one of <1> to <3>, wherein the component (A) is preferably at least any one selected from the group consisting of lauric acid, myristic acid, palmitic acid, stearic acid, and behenic acid, more preferably at least any one selected from the group consisting of palmitic acid and stearic acid.

<5> The skin cosmetic according to any one of <1> to <4>, wherein the content of the component (A) in the whole composition is preferably 1.5 mass % or more, more preferably 2.5 mass % or more, and is preferably 6 mass % or less, more preferably 5 mass % or less.

<6> The skin cosmetic according to any one of <1> to <5>, wherein the component (B) preferably contains at least any one or more of alkylamines selected from the group consisting of methylamine, ethylamine, propylamine, butylamine, hexylamine, dimethylamine, and diethylamine; alkanolamines selected from the group consisting of monoethanolamine, diethanolamine, triethanolamine, N-methyl-diethanolamine, N,N-dimethyl monoethanolamine, and aminomethyl propanol; and basic amino acids selected from the group consisting of lysine, histidine, and arginine.

<7> The skin cosmetic according to any one of <1> to <6>, wherein the component (B) is preferably an alkanolamine having an alkyl group having 1 to 6 of carbon atom or a basic amino acid having 1 to 6 of carbon atom, more preferably an alkanolamine having an alkyl group having 3 to 6 of carbon atom or a basic amino acid having 3 to 6 of carbon atom, further preferably a basic amino acid.

<8> The skin cosmetic according to any one of <1> to <7>, wherein the component (B) is preferably aminomethyl propanol or arginine, more preferably arginine, wherein the arginine is preferably L-arginine.

<9> The skin cosmetic according to any one of <1> to <8>, wherein the content of the component (B) in the whole composition is preferably 0.1 mass % or more, more preferably 0.2 mass % or more, and is preferably 2.5 mass % or less, more preferably 1.8 mass % or less.

<10> The skin cosmetic according to any one of <1> to <9>, wherein the component (C) is preferably sodium hydroxide or potassium hydroxide.

<11> The skin cosmetic according to any one of <1> to <10>, wherein the content of the component (C) in the whole composition is preferably 0.1 mass % or more, more preferably 0.2 mass % or more, and is preferably 0.75 mass % or less, more preferably 0.6 mass % or less.

<12> The skin cosmetic according to any one of <1> to <11>, wherein the molar ratio of the component (C) to the total amount of the components (B) and (C) [(B)+(C)], (B)/[(B)+(C)], is preferably (B)/[(B)+(C)]=from 10 to 40 mol %, more preferably from 15 to 30 mol %.

<13> The skin cosmetic according to any one of <1> to <12>, wherein the molar ratio of the total amount of the components (B) and (C) [(B)+(C))] to the component (A), [(B)+(C)]/(A), is preferably [(B)+(C)]/(A)=from 90 to 100 mol %, more preferably from 95 to 100 mol %.

<14> The skin cosmetic according to any one of <1> to <13>, wherein the combination of the component (B) and the component (C) is preferably aminomethyl propanol or arginine as the component (B) and sodium hydroxide or potassium hydroxide as the component (C), more preferably arginine as the component (B) and sodium hydroxide as the component (C).

<15> The skin cosmetic according to any one of <1> to <14>, wherein the component (D) is preferably a linear saturated alcohol having 14 to 22 of carbon atom, more preferably a linear saturated alcohol having 16 to 22 of carbon atom.

<16> The skin cosmetic according to any one of <1> to <15>, wherein the component (D) preferably contains at least any one selected from the group consisting of lauryl alcohol, myristyl alcohol, cetyl alcohol, stearyl alcohol, and behenyl alcohol, more preferably at least any one selected from the group consisting of cetyl alcohol and stearyl alcohol, further preferably cetyl alcohol and stearyl alcohol.

<17> The skin cosmetic according to any one of <1> to <16>, wherein the content of the component (D) in the whole composition is preferably 1.5 mass % or more, more preferably 2.5 mass % or more, and is preferably 6 mass % or less, more preferably 5 mass % or less.
<18> The skin cosmetic according to any one of <1> to <16>, wherein the content of the component (D) in the whole composition is preferably 0.6 mass % or more, more preferably 0.8 mass % or more, further preferably 1.5 mass % or more, still further preferably 2.5 mass % or more, and is preferably 6.5 mass % or less, more preferably 6 mass % or less, further preferably 5.5 mass % or less, still further preferably 5 mass % or less.
<19> The skin cosmetic according to any one of <1> to <18>, wherein the total amount of the components (A) and (D), (A)+(D), in the whole composition is preferably 3.5 mass % or more, more preferably 4.5 mass % or more, and is preferably 12 mass % or less, more preferably 10 mass % or less.
<20> The skin cosmetic according to any one of <1> to <19>, wherein the mass ratio of the component (A) to the total amount of the components (A) and (D) [(A)+(D)], {(A)/[(A)+(D)]}, is preferably 0.2 or more, more preferably 0.3 or more, and is preferably 0.8 or less, more preferably 0.7 or less.
<21> The skin cosmetic according to any one of <1> to <20>, wherein the component (E) is preferably at least one or more selected from the group consisting of a hydrocarbon oil, an ether oil, an ester oil, a silicone oil, and a fluorinated oil, more preferably a hydrocarbon oil, an ester oil, or a silicone oil, wherein the hydrocarbon oil is preferably at least one selected from the group consisting of liquid paraffin, squalane, and Vaseline, the ester oil is preferably at least one selected from the group consisting of octyldodecyl myristate, isopropyl palmitate, butyl stearate, di-2-ethylhexyl adipate, neopentyl glycol dicaprate, trioctanoin, and benzoic acid alkyl ester, and the silicone oil is preferably at least one selected from the group consisting of dimethylpolysiloxane, cyclic dimethylpolysiloxane, methylphenylpolysiloxane, amino-modified silicone, carboxy-modified silicone, alcohol-modified silicone, alkyl-modified silicone, polyether-modified silicone, and fluorine-modified silicone.
<22> The skin cosmetic according to any one of <1> to <21>, wherein the component (E) is preferably an oil agent having an SP value of from 16.0 to 21.0, more preferably an SP value of from 17.0 to 20.0, further preferably an SP value of from 18.0 to 19.0.
<23> The skin cosmetic according to <22>, wherein the oil agent having an SP value of 16.0 to 21.0 is preferably isopropyl palmitate (SP value: 17.0), neopentyl glycol dicaprate (SP value: 17.7), 2-ethylhexyl 4-methoxycinnamate (SP value: 19.0), polyglyceryl-2 diisostearate (SP value: 20.5), alkyl benzoate (C12-C15) (SP value: 18.0 to 18.2), triethylhexanoin (SP value: 18.1), or dimethicone (10 cs) (SP value: 17), more preferably at least any one selected from the group consisting of isopropyl palmitate (SP value: 17.0), alkyl benzoate (C12-C15) (SP value: 18.0 to 18.2), dimethicone (10 cs) (SP value: 17), and triethylhexanoin (SP value: 18.1), further preferably alkyl benzoate (C12-C15) or triethylhexanoin.
<24> The skin cosmetic according to any one of <1> to <23>, wherein the content of the component (E) in the whole composition is preferably 0.5 mass % or more, more preferably 3 mass % or more, and is preferably 15 mass % or less, more preferably 10 mass % or less.
<25> The skin cosmetic according to any one of <1> to <24>, wherein the mass ratio of the component (E) to the total amount of the components (A) and (D) [(A)+(D)], {(E)/[(A)+(D)]}, is preferably 0.1 or more, more preferably 0.2 or more, further preferably 0.3 or more, and is preferably 3 or less, more preferably 2 or less, further preferably 1.5 or less.
<26> The skin cosmetic according to any one of <1> to <25>, wherein the content of water as the component (F) in the whole composition is preferably 50 mass % or more, more preferably 60 mass % or more, and is preferably 95 mass % or less, more preferably 90 mass % or less.
<27> The skin cosmetic according to any one of <1> to <26>, further containing (G) a nonionic surfactant, wherein the content thereof in the whole composition is preferably 0.1 mass % or more, more preferably 0.3 mass % or more, further preferably 0.5 mass % or more, and is preferably 2 mass % or less, more preferably 1.8 mass % or less, further preferably 1.5 mass % or less.
<28> The skin cosmetic according to <27>, wherein the nonionic surfactant (G) is preferably one or more selected from the group consisting of an ethylene glycol fatty acid ester, a polyethylene glycol fatty acid ester, a polyalkylene glycol alkyl ether, a polyethylene glycol hydrogenated castor oil, a propylene glycol fatty acid ester, a monoglycerin monofatty acid ester, a monoglycerin difatty acid ester, a glycerin alkyl ether, a sorbitan fatty acid ester, a fatty acid alkanolamide, and a fatty acid dialkanolamide, more preferably a polyalkylene glycol alkyl ether, further preferably a polyalkylene glycol alkyl ether having an alkyl group having 12 to 22 of carbon atom, still further preferably a polyalkylene glycol alkyl ether having an alkyl group having 12 to 18 of carbon atom.
<29> The skin cosmetic according to <27> or <28>, wherein the nonionic surfactant (G) preferably contains at least two polyalkylene glycol ethers differing in the number of carbon atom in their alkyl groups by 2 or more, more preferably contains at least two selected from the group consisting of polyethylene glycol ether of lauryl alcohol (laureth-3), polyethylene glycol ether of cetyl alcohol, and polyethylene glycol ether of stearyl alcohol, further preferably contains these 3 polyethylene glycol ethers, and still further preferably contains laureth-3 and ceteareth-20.
<30> The skin cosmetic according to any one of <27> to <29>, wherein the mass ratio of the total amount of the components (A) and (D) [(A)+(D)] to the component (G), {[(A)+(D)]/G}, is preferably 3 or more, more preferably 4 or more, further preferably 5 or more, and preferably 30 or less, more preferably 20 or less, further preferably 15 or less.
<31> The skin cosmetic according to any one of <1> to <30>, further containing (H) an ionic surfactant, wherein the content thereof in the whole composition is preferably 0.01 mass % or more, more preferably 0.1 mass % or more, further preferably 0.3 mass % or more, and is preferably 2 mass % or less, more preferably 1.8 mass % or less, further preferably 1.5 mass % or less.
<32> The skin cosmetic according to <31>, wherein the ionic surfactant (H) is preferably an anionic surfactant, more preferably one or two or more selected from the group consisting of an alkyl ether phosphate having 12 to 22 of carbon atom of polyoxyethylene or a salt thereof, sodium N-alkyloyl methyltaurine having 12 to 22 of carbon atom, and a N-acyl glutamate having 12 to 22 of carbon atom, further preferably an alkyl ether phosphate having 12 to 22 of carbon atom of polyoxyethylene or a salt thereof.

<33> The skin cosmetic according to <32>, wherein the content of the anionic surfactant in the whole composition is preferably 0.01 mass % or more, more preferably 0.1 mass % or more, further preferably 0.3 mass % or more, and is preferably 2 mass % or less, more preferably 1.8 mass % or less, further preferably 1.5 mass % or less.

<34> The skin cosmetic according to any one of <31> to <33>, wherein the mass ratio of the component (H) to the total amount of the components (G) and (H) [(G)+(H)], {(H)/[(G)+(H)]}, is preferably 0.01 or more, more preferably 0.1 or more, further preferably 0.2 or more, and is preferably 0.75 or less, more preferably 0.6 or less, further preferably 0.5 or less.

<35> The skin cosmetic according to any one of <1> to <34>, wherein the skin cosmetic has a pH of preferably from 5.5 to 9.5, more preferably from 6.0 to 9.0, further preferably from 6.5 to 8.5, at 25° C.

<36> The skin cosmetic according to any one of <1> to <35>, wherein the skin cosmetic has a bulk lamellar structure and a concentric lamellar structure.

<37> The skin cosmetic according to any one of <1> to <36>, wherein the content of a solid fat other than the components (A) and (D) in the whole composition is preferably 10 mass % or less, more preferably 8 mass % or less, further preferably 5 mass % or less, still further preferably 3 mass % or less.

<38> A method for using a skin cosmetic, including using a skin cosmetic according to any one of <1> to <37> to the skin, preferably applying a skin cosmetic according to any one of <1> to <37> to the skin except for the scalp, more preferably any of the face, the body, limbs, and the like.

<39> A moisturizing method containing applying a skin cosmetic according to any one of <1> to <37> to the skin.

<40> A glossing method including applying a skin cosmetic according to any one of <1> to <37> to the skin.

<41> A method for producing a skin cosmetic according to any one of <1> to <37>, including steps 1 to 3:

step 1: the step of mixing the components (B), (C), and (F) and homogeneously dissolving the mixture at 60 to 100° C. to form an aqueous phase portion, step 2: the step of mixing the components (A), (D), and (E) and homogeneously dissolving the mixture at 60 to 100° C. to form an oil phase portion, and step 3: the step of homogeneously mixing the aqueous phase portion obtained in step 1 with the oil phase portion obtained in step 2 and cooling the mixture to preferably from 5 to 30° C., more preferably from 10 to 28° C., further preferably from 15 to 26° C.

EXAMPLES

Examples 1 to 39 and Comparative Examples 1 to 10

Skin cosmetics were produced according to the composition shown in Tables 1 to 4, and the presence or absence of concentric lamella formation in the cosmetics and dried films was observed. The skin cosmetics were evaluated for moisturizing properties (moisture-confining properties), an oily feel, the sustention of the softness of the skin, the sustention of gloss, and the suppression of oil separation at 50° C. The results are also shown in Tables 1 to 4.

(Production Method)

The aqueous phase components including the components (B), (C), and (F) were dissolved by stirring at 70 to 80° C. to form an aqueous phase portion. Next, the oil phase components including the components (A), (D), and (E) were dissolved by stirring at 70 to 80° C. to form an oil phase portion. The oil phase portion was added to the aqueous phase portion with stirring at 70 to 80° C., and the mixture was cooled to room temperature (25° C.) with further stirring to produce a skin cosmetic (oil-in-water emulsion cosmetic).

(Evaluation Method)

(1) Confirmation of Concentric Lamella:

The cosmetics and dried films were evaluated for their phase states. Each dried film was prepared by spreading 1 g of each cosmetic at a thickness of 0.1 mm using an applicator and drying the resulting film at 20° C. for 24 hours in a 20% RH environment.

The samples (thickness: 25 mm) were observed under a polarization microscope (×200). A sample confirmed to have maltese cross around oil droplets was indicated by "Y" (concentric lamella was present), and a sample confirmed not to have maltese cross or confirmed to have maltese cross but to also have crystals was indicated by "N".

(2) Moisturizing Properties (Moisture-Confining Properties):

Each cosmetic was applied at 0.01 mL/cm$^2$ to 5C quantitative filter paper (manufactured by Toyo Roshi Kaisha, Ltd., ADVANTEC FILTER PAPER 5C) and left to stand at 20° C. for 24 hours in a 20% RH environment. A portion of this filter paper was cut out and placed on a 40-mL vial (Pierce Vial CV-400, manufactured by AS ONE Corp.; the lid has an opening of 17.3 mm in diameter) to cover the top of the vial therewith. A given amount of water was added to the vial, and the resulting vial was left to stand at 20° C. for 24 hours in a 20% RH environment. The amount of water decreased was measured.

The mass before storage was defined as m1; the mass after 24 hours was defined as m2; the amount of water evaporation in the case of cosmetic-unapplied filter paper was defined as W (g); and the amount of water evaporation in the case where the cosmetic of each Example or Comparative Example was applied to the filter paper was defined as S (g). The rate of suppression of water evaporation (%) was determined according to the following expressions:

Amount of water evaporation $W(g)=Wm1-Wm2$

Amount of water evaporation $S(g)=Sm1-Sm2$

Rate of suppression of water evaporation $(\%)=(W(g)-S(g))/W(g)\times 100$

A higher numeric value represents better moisturizing properties (moisture-confining properties).

(3) Oily Feel:

Ten expert panelists uniformly applied 2 mg/cm$^2$ of each skin cosmetic on their faces and conducted sensory evaluation on an oily feel according to the following criteria, and an average of the scores was determined.

4: Non-sticky.
3: Slightly non-sticky.
2: Slightly oily.
1: Very oily.

(4) Sustention of Softness of Skin:

Ten expert panelists uniformly applied 2 mg/cm$^2$ of each skin cosmetic on their faces after face wash and conducted sensory evaluation on the softness of the skin 3 hours later according to the following criteria, and an average of the scores was determined.

4: Very soft.
3: Slightly soft.
2: Slightly stiffened.
1: Very stiffened.

(5) Sustention of Gloss:

Ten expert panelists uniformly applied 2 mg/cm² of each skin cosmetic on their faces and conducted sensory evaluation on the gloss of the skin after a lapse of 3 hours according to the following criteria, and an average of the scores was determined.
4: A lot of gloss feel.
3: Slight gloss feel.
2: Almost no gloss feel.
1: No gloss feel and a matte feel instead.

(6) Suppression of oil separation at 50° C.:

After storage of each skin cosmetic at 50° C. for 1 month, its oil separation state was visually observed and evaluated according to the following criteria.
4: No oil separation was observed.
3: Oil separation of less than approximately 1 mm on the surface was observed.
2: Oil separation of approximately 1 mm or more and less than 5 mm on the surface was observed.
1: Water separation of approximately 5 mm or more and less than 10 mm on the surface was observed.

TABLE 1

| | Component (mass %) | Example 1 | 2 | 3 | 4 | 5 | 6 | 7 |
|---|---|---|---|---|---|---|---|---|
| A | Myristic acid | | | | | | | |
| | Stearic acid | 0.5 | 2.8 | 7.0 | 1.0 | 7.0 | 1.5 | 6.0 |
| | Behenic acid | | | | | | | |
| B | L-arginine | 0.02 | 0.15 | 1.50 | 0.04 | 1.60 | 0.04 | 2.00 |
| | 2-Amino-2-methyl-1-propanol | | | | | | | |
| | Triethanolamine | | | | | | | |
| C | Sodium hydroxide | 0.06 | 0.4 | 0.70 | 0.15 | 0.52 | 0.16 | 0.55 |
| | Potassium hydroxide | | | | | | | |
| D | Myristyl alcohol | | | | | | | |
| | Stearyl alcohol | | | | | | | |
| | Cetostearyl alcohol | 1.8 | 0.7 | 6.2 | 6.5 | 1.0 | 5.2 | 2.0 |
| | Behenyl alcohol | | | | | | | |
| E | Alkyl benzoate (C12-C15) | 0.3 | 3.0 | 20.0 | 0.8 | 20.0 | 0.8 | 20.0 |
| | Isopropyl palmitate | | | | | | | |
| | Mineral oil | | | | | | | |
| | Silicone oil (200 cs) | | | | | | | |
| | Triethylhexanoin | | | | | | | |
| F | Water | Balance | Balance | Balance | Balance | Balance | Balance | Balance |
| G | Ceteareth-20 (HLB 12.0) | | | | | | | |
| | Laureth-3 (HLB 7.0) | | | | | | | |
| | Glycerin monostearic acid ester (HLB3.4) | | | | | | | |
| | PEG-30 hydrogenated castor oil (HLB 11.0) | | | | | | | |
| H | Sodium lauryl ether phosphate (SPE-104NB) | | | | | | | |
| | Sodium stearoyl methyltaurine (NIKKOL SMT) | | | | | | | |
| | Sodium N-stearoyl-L-glutamate (AMISOFT HS-11P) | | | | | | | |
| | Total | 100.0 | 100.0 | 100.0 | 100.0 | 100.0 | 100.0 | 100.0 |
| | A + D | 2.3 | 3.5 | 13.2 | 7.5 | 8.0 | 6.7 | 8.0 |
| | A/(A + D) Mass ratio | 0.22 | 0.80 | 0.53 | 0.13 | 0.88 | 0.22 | 0.75 |
| | B/(B + C) Molar ratio (mol %) | 7.7 | 32.9 | 5.8 | 41.4 | 5.4 | 45.5 | |
| | (B + C)/A Molar ratio (mol %) | 84.8 | 110.4 | 106.1 | 113.2 | 90.2 | 80.2 | 119.6 |
| | (A + D)/G Mass ratio | — | — | — | — | — | — | — |
| | E/(A + D) Mass ratio | 0.13 | 0.86 | 1.52 | 0.11 | 2.50 | 0.12 | 2.50 |
| | H/(G + H) Mass ratio | — | — | — | — | — | — | — |
| | Concentric lamella (preparation) | Y | Y | Y | Y | Y | Y | Y |
| | Concentric lamella (coating film) | Y | Y | Y | Y | Y | Y | Y |
| | Moisturizing properties (moisture-confining properties) | 31 | 35 | 36 | 34 | 38 | 37 | 43 |
| | Oily feel | 2.2 | 2.4 | 1.8 | 2.3 | 1.8 | 2.5 | 1.9 |
| | Sustention of softness of skin | 1.8 | 2.1 | 2.2 | 1.9 | 2.3 | 1.9 | 2.4 |
| | Sustention of gloss | 1.9 | 2.0 | 2.1 | 1.8 | 2.0 | 1.8 | 1.9 |
| | Suppression of oil separation at 50° C. | 2 | 2 | 2 | 2 | 2 | 2 | 2 |

| | Component (mass %) | Example 8 | 9 | 10 | 11 | 12 | 13 |
|---|---|---|---|---|---|---|---|
| A | Myristic acid | | | | | | |
| | Stearic acid | 1.5 | 6.0 | 3.0 | 4.0 | 3.5 | 3.5 |
| | Behenic acid | | | | | | |
| B | L-arginine | 0.07 | 1.50 | 0.20 | 0.80 | 0.35 | 0.35 |
| | 2-Amino-2-methyl-1-propanol | | | | | | |
| | Triethanolamine | | | | | | |
| C | Sodium hydroxide | 0.16 | 0.55 | 0.30 | 0.45 | 0.40 | 0.40 |
| | Potassium hydroxide | | | | | | |
| D | Myristyl alcohol | | | | | | |
| | Stearyl alcohol | | | | | | |
| | Cetostearyl alcohol | 2.0 | 6.0 | 3.2 | 3.5 | 3.0 | 3.0 |
| | Behenyl alcohol | | | | | | |

TABLE 1-continued

|   | Component | | | | | | |
|---|---|---|---|---|---|---|---|
| E | Alkyl benzoate (C12-C15) | 0.6 | 20.0 | 0.8 | 20.0 | 0.8 | 18.0 |
|   | Isopropyl palmitate | | | | | | |
|   | Mineral oil | | | | | | |
|   | Silicone oil (200 cs) | | | | | | |
|   | Triethylhexanoin | | | | | | |
| F | Water | Balance | Balance | Balance | Balance | Balance | Balance |
| G | Ceteareth-20 (HLB 12.0) | | | | | | |
|   | Laureth-3 (HLB 7.0) | | | | | | |
|   | Glycerin monostearic acid ester (HLB3.4) | | | | | | |
|   | PEG-30 hydrogenated castor oil (HLB 11.0) | | | | | | |
| H | Sodium lauryl ether phosphate (SPE-104NB) | | | | | | |
|   | Sodium stearoyl methyltaurine (NIKKOL SMT) | | | | | | |
|   | Sodium N-stearoyl-L-glutamate (AMISOFT HS-11P) | | | | | | |
|   | Total | 100.0 | 100.0 | 100.0 | 100.0 | 100.0 | 100.0 |
|   | A + D | 3.5 | 12.0 | 6.2 | 7.5 | 6.5 | 6.5 |
|   | A/(A + D) Mass ratio | 0.43 | 0.50 | 0.48 | 0.53 | 0.54 | 0.54 |
|   | B/(B + C) Molar ratio (mol %) | 9.1 | 38.5 | 13.3 | 29.0 | 16.7 | 16.7 |
|   | (B + C)/A Molar ratio (mol %) | 83.5 | 106.0 | 82.0 | 112.7 | 97.6 | 97.6 |
|   | (A + D)/G Mass ratio | — | — | — | — | — | — |
|   | E/(A + D) Mass ratio | 0.17 | 1.67 | 0.13 | 2.67 | 0.12 | 2.77 |
|   | H/(G + H) Mass ratio | — | — | — | — | — | — |
|   | Concentric lamella (preparation) | Y | Y | Y | Y | Y | Y |
|   | Concentric lamella (coating film) | Y | Y | Y | Y | Y | Y |
|   | Moisturizing properties (moisture-confining properties) | 40 | 48 | 42 | 45 | 44 | 49 |
|   | Oily feel | 2.6 | 1.9 | 2.6 | 2.1 | 2.7 | 2.2 |
|   | Sustention of softness of skin | 2.1 | 2.6 | 2.1 | 2.6 | 2.8 | 3.4 |
|   | Sustention of gloss | 2.0 | 1.8 | 2.2 | 2.5 | 2.6 | 2.5 |
|   | Suppression of oil separation at 50° C. | 2 | 2 | 2 | 2 | 3 | 3 |

TABLE 2

|   | Component (mass %) | Example | | | | | | |
|---|---|---|---|---|---|---|---|---|
|   |   | 14 | 15 | 16 | 17 | 18 | 19 | 20 |
| A | Myristic acid | | | 3.0 | | | | |
|   | Stearic acid | 3.5 | 4.0 | | 3.3 | | 3.5 | 3.5 |
|   | Behenic acid | | | | | 4.8 | | |
| B | L-arginine | 0.35 | 0.50 | 0.60 | 0.40 | 0.45 | | |
|   | 2-Amino-2-methyl-1-propanol | | | | | | 0.35 | |
|   | Triethanolamine | | | | | | | 0.28 |
| C | Sodium hydroxide | 0.40 | 0.40 | 0.38 | 0.35 | 0.45 | 0.40 | 0.40 |
|   | Potassium hydroxide | | | | | | | |
| D | Myristyl alcohol | | | 4.00 | | | | |
|   | Stearyl alcohol | | | | 4.00 | | | |
|   | Cetostearyl alcohol | 3.0 | 4.0 | | | | 3.0 | 3.0 |
|   | Behenyl alcohol | | | | | 5.0 | | |
| E | Alkyl benzoate (C12-C15) | 5.0 | 12.0 | 6.0 | 8.0 | 10.0 | 5.0 | 5.0 |
|   | Isopropyl palmitate | | | | | | | |
|   | Mineral oil | | | | | | | |
|   | Silicone oil (200 cs) | | | | | | | |
|   | Triethylhexanoin | | | | | | | |
| F | Water | Balance | Balance | Balance | Balance | Balance | Balance | Balance |
| G | Ceteareth-20 (HLB 12.0) | | | | | | | |
|   | Laureth-3 (HLB 7.0) | | | | | | | |
|   | Glycerin monostearic acid ester (HLB3.4) | | | | | | | |
|   | PEG-30 hydrogenated castor oil (HLB 11.0) | | | | | | | |
| H | Sodium lauryl ether phosphate (SPE-104NB) | | | | | | | |
|   | Sodium stearoyl methyltaurine (NIKKOL SMT) | | | | | | | |
|   | Sodium N-stearoyl-L-glutamate (AMISOFT HS-11P) | | | | | | | |
|   | Total | 100.0 | 100.0 | 100.0 | 100.0 | 100.0 | 100.0 | 100.0 |
|   | A + D | 6.5 | 8.0 | 7.0 | 7.3 | 9.8 | 6.5 | 6.5 |
|   | A/(A + D) Mass ratio | 0.54 | 0.50 | 0.43 | 0.45 | 0.49 | 0.54 | 0.54 |
|   | B/(B + C) Molar ratio (mol %) | 16.7 | 22.3 | 26.6 | 20.8 | 18.6 | 28.2 | 15.8 |
|   | (B + C)/A Molar ratio (mol %) | 97.6 | 91.5 | 98.5 | 95.2 | 98.2 | 97.6 | 96.5 |
|   | (A + D)/G Mass ratio | — | — | — | — | — | — | — |
|   | E/(A + D) Mass ratio | 0.77 | 1.50 | 0.86 | 1.10 | 1.02 | 0.77 | 0.77 |
|   | H/(G + H) Mass ratio | — | — | — | — | — | — | — |
|   | Concentric lamella (preparation) | Y | Y | Y | Y | Y | Y | Y |

TABLE 2-continued

| | | | | | | | |
|---|---|---|---|---|---|---|---|
| Concentric lamella (coating film) | Y | Y | Y | Y | Y | Y | Y |
| Moisturizing properties (moisture-confining properties) | 51 | 55 | 45 | 48 | 53 | 43 | 45 |
| Oily feel | 3.1 | 3.0 | 2.8 | 3.0 | 3.1 | 3.0 | 3.0 |
| Sustention of softness of skin | 3.0 | 3.5 | 3.0 | 3.0 | 2.9 | 2.9 | 2.8 |
| Sustention of gloss | 2.8 | 3.0 | 2.8 | 2.8 | 2.7 | 2.7 | 2.9 |
| Suppression of oil separation at 50° C. | 3 | 3 | 3 | 3 | 3 | 3 | 3 |

| | Component (mass %) | Example 21 | Example 22 | Example 23 | Example 24 | Example 25 |
|---|---|---|---|---|---|---|
| A | Myristic acid | | | | | |
| | Stearic acid | 3.5 | 3.5 | 3.5 | 3.5 | 3.5 |
| | Behenic acid | | | | | |
| B | L-arginine | 0.45 | 0.35 | 0.35 | 0.35 | 0.35 |
| | 2-Amino-2-methyl-1-propanol | | | | | |
| | Triethanolamine | | | | | |
| C | Sodium hydroxide | | 0.40 | 0.40 | 0.40 | 0.40 |
| | Potassium hydroxide | 0.54 | | | | |
| D | Myristyl alcohol | | | | | |
| | Stearyl alcohol | | | | | |
| | Cetostearyl alcohol | 3.0 | 3.0 | 3.0 | 3.0 | 3.0 |
| | Behenyl alcohol | | | | | |
| E | Alkyl benzoate (C12-C15) | 5.0 | | | | |
| | Isopropyl palmitate | | 5.0 | | | |
| | Mineral oil | | | 5.0 | | |
| | Silicone oil (200 cs) | | | | 5.0 | |
| | Triethylhexanoin | | | | | 5.0 |
| F | Water | Balance | Balance | Balance | Balance | Balance |
| G | Ceteareth-20 (HLB 12.0) | | | | | |
| | Laureth-3 (HLB 7.0) | | | | | |
| | Glycerin monostearic acid ester (HLB3.4) | | | | | |
| | PEG-30 hydrogenated castor oil (HLB 11.0) | | | | | |
| H | Sodium lauryl ether phosphate (SPE-104NB) | | | | | |
| | Sodium stearoyl methyltaurine (NIKKOL SMT) | | | | | |
| | Sodium N-stearoyl-L-glutamate (AMISOFT HS-11P) | | | | | |
| | Total | 100.0 | 100.0 | 100.0 | 100.0 | 100.0 |
| | A + D | 6.5 | 6.5 | 6.5 | 6.5 | 6.5 |
| | A/(A + D) Mass ratio | 0.54 | 0.54 | 0.54 | 0.54 | 0.54 |
| | B/(B + C) Molar ratio (mol %) | 21.1 | 16.7 | 16.7 | 16.7 | 16.7 |
| | (B + C)/A Molar ratio (mol %) | 99.2 | 97.6 | 97.6 | 97.6 | 97.6 |
| | (A + D)/G Mass ratio | — | — | — | — | — |
| | E/(A + D) Mass ratio | 0.77 | 0.77 | 0.77 | 0.77 | 0.77 |
| | H/(G + H) Mass ratio | — | — | — | — | — |
| | Concentric lamella (preparation) | Y | Y | Y | Y | Y |
| | Concentric lamella (coating film) | Y | Y | Y | Y | Y |
| | Moisturizing properties (moisture-confining properties) | 50 | 45 | 44 | 43 | 53 |
| | Oily feel | 3.1 | 3.0 | 2.9 | 2.8 | 3.0 |
| | Sustention of softness of skin | 3.0 | 3.0 | 3.0 | 2.9 | 3.1 |
| | Sustention of gloss | 2.9 | 2.6 | 2.4 | 2.4 | 3.0 |
| | Suppression of oil separation at 50° C. | 3 | 3 | 3 | 3 | 3 |

TABLE 3

| | Component (mass %) | Example 26 | Example 27 | Example 28 | Example 29 | Example 30 | Example 31 | Example 32 |
|---|---|---|---|---|---|---|---|---|
| A | Myristic acid | | | | | | | |
| | Stearic acid | 3.5 | 3.5 | 3.5 | 3.5 | 3.5 | 3.5 | 3.5 |
| | Behenic acid | | | | | | | |
| B | L-arginine | 0.35 | 0.35 | 0.35 | 0.35 | 0.35 | 0.35 | 0.35 |
| | 2-Amino-2-methyl-1-propanol | | | | | | | |
| | Triethanolamine | | | | | | | |
| C | Sodium hydroxide | 0.40 | 0.40 | 0.40 | 0.40 | 0.40 | 0.40 | 0.40 |
| | Potassium hydroxide | | | | | | | |
| D | Myristyl alcohol | | | | | | | |
| | Stearyl alcohol | | | | | | | |
| | Cetostearyl alcohol | 3.0 | 3.0 | 3.0 | 3.0 | 3.0 | 3.0 | 3.0 |
| | Behenyl alcohol | | | | | | | |
| E | Alkyl benzoate (C12-C15) | 5.0 | 5.0 | 5.0 | 5.0 | 5.0 | 5.0 | 5.0 |
| | Isopropyl palmitate | | | | | | | |
| | Mineral oil | | | | | | | |
| | Silicone oil (200 cs) | | | | | | | |
| | Triethylhexanoin | | | | | | | |

TABLE 3-continued

|   | Component (mass %) | | | | | | | |
|---|---|---|---|---|---|---|---|---|
| F | Water | Balance | Balance | Balance | Balance | Balance | Balance | Balance |
| G | Ceteareth-20 (HLB 12.0) | 0.3 | 2.0 | 0.7 | 1.3 | | | |
|   | Laureth-3 (HLB 7.0) | | | | | 1.0 | | |
|   | Glycerin monostearic acid ester (HLB3.4) | | | | | | 1.0 | |
|   | PEG-30 hydrogenated castor oil (HLB 11.0) | | | | | | | 1.0 |
| H | Sodium lauryl ether phosphate (SPE-104NB) | | | | | | | |
|   | Sodium stearoyl methyltaurine (NIKKOL SMT) | | | | | | | |
|   | Sodium N-stearoyl-L-glutamate (AMISOFT HS-11P) | | | | | | | |
|   | Total | 100.0 | 100.0 | 100.0 | 100.0 | 100.0 | 100.0 | 100.0 |
|   | A + D | 6.5 | 6.5 | 6.5 | 6.5 | 6.5 | 6.5 | 6.5 |
|   | A/(A + D) Mass ratio | 0.54 | 0.54 | 0.54 | 0.54 | 0.54 | 0.54 | 0.54 |
|   | B/(B + C) Molar ratio (mol %) | 16.7 | 16.7 | 16.7 | 16.7 | 16.7 | 16.7 | 16.7 |
|   | (B + C)/A Molar ratio (mol %) | 97.6 | 97.6 | 97.6 | 97.6 | 97.6 | 97.6 | 97.6 |
|   | (A + D)/G Mass ratio | 26.0 | 3.3 | 9.3 | 5.0 | 6.5 | 6.5 | 6.5 |
|   | E/(A + D) Mass ratio | 0.77 | 0.77 | 0.77 | 0.77 | 0.77 | 0.77 | 0.77 |
|   | H/(G + H) Mass ratio | — | — | — | — | — | — | — |
|   | Concentric lamella (preparation) | Y | Y | Y | Y | Y | Y | Y |
|   | Concentric lamella (coating film) | Y | Y | Y | Y | Y | Y | Y |
|   | Moisturizing properties (moisture-confining properties) | 54 | 51 | 55 | 54 | 56 | 55 | 50 |
|   | Oily feel | 3.3 | 3.2 | 3.4 | 3.4 | 3.4 | 3.4 | 3.4 |
|   | Sustention of softness of skin | 3.4 | 3.4 | 3.5 | 3.4 | 3.5 | 3.4 | 3.5 |
|   | Sustention of gloss | 3.1 | 3.2 | 3.4 | 3.4 | 3.4 | 3.4 | 3.2 |
|   | Suppression of oil separation at 50° C. | 4 | 4 | 4 | 4 | 4 | 4 | 4 |

|   | | Example | | | | |
|---|---|---|---|---|---|---|
|   | Component (mass %) | 33 | 34 | 35 | 36 | 37 |
| A | Myristic acid | | | | | |
|   | Stearic acid | 3.5 | 3.5 | 3.5 | 3.5 | 3.5 |
|   | Behenic acid | | | | | |
| B | L-arginine | 0.35 | 0.35 | 0.35 | 0.35 | 0.35 |
|   | 2-Amino-2-methyl-1-propanol | | | | | |
|   | Triethanolamine | | | | | |
| C | Sodium hydroxide | 0.40 | 0.40 | 0.40 | 0.40 | 0.40 |
|   | Potassium hydroxide | | | | | |
| D | Myristyl alcohol | | | | | |
|   | Stearyl alcohol | | | | | |
|   | Cetostearyl alcohol | 3.0 | 3.0 | 3.0 | 3.0 | 3.0 |
|   | Behenyl alcohol | | | | | |
| E | Alkyl benzoate (C12-C15) | 5.0 | 5.0 | 5.0 | 5.0 | 5.0 |
|   | Isopropyl palmitate | | | | | |
|   | Mineral oil | | | | | |
|   | Silicone oil (200 cs) | | | | | |
|   | Triethylhexanoin | | | | | |
| F | Water | Balance | Balance | Balance | Balance | Balance |
| G | Ceteareth-20 (HLB 12.0) | 0.5 | 0.5 | 0.5 | 0.5 | 0.5 |
|   | Laureth-3 (HLB 7.0) | 0.5 | 0.5 | 0.5 | 0.5 | 0.5 |
|   | Glycerin monostearic acid ester (HLB3.4) | | | | | |
|   | PEG-30 hydrogenated castor oil (HLB 11.0) | | | | | |
| H | Sodium lauryl ether phosphate (SPE-104NB) | | 0.1 | 1.0 | 0.5 | |
|   | Sodium stearoyl methyltaurine (NIKKOL SMT) | | | | | 0.5 |
|   | Sodium N-stearoyl-L-glutamate (AMISOFT HS-11P) | | | | | |
|   | Total | 100.0 | 100.0 | 100.0 | 100.0 | 100.0 |
|   | A + D | 6.5 | 6.5 | 6.5 | 6.5 | 6.5 |
|   | A/(A + D) Mass ratio | 0.54 | 0.54 | 0.54 | 0.54 | 0.54 |
|   | B/(B + C) Molar ratio (mol %) | 16.7 | 16.7 | 16.7 | 16.7 | 16.7 |
|   | (B + C)/A Molar ratio (mol %) | 97.6 | 97.6 | 97.6 | 97.6 | 97.6 |
|   | (A + D)/G Mass ratio | 6.5 | 6.5 | 6.5 | 6.5 | 6.5 |
|   | E/(A + D) Mass ratio | 0.77 | 0.77 | 0.77 | 0.77 | 0.77 |
|   | H/(G + H) Mass ratio | — | 0.05 | 0.50 | 0.33 | 0.00 |
|   | Concentric lamella (preparation) | Y | Y | Y | Y | Y |
|   | Concentric lamella (coating film) | Y | Y | Y | Y | Y |
|   | Moisturizing properties (moisture-confining properties) | 56 | 57 | 58 | 61 | 63 |
|   | Oily feel | 3.5 | 3.6 | 3.8 | 3.8 | 3.8 |
|   | Sustention of softness of skin | 3.6 | 3.8 | 3.8 | 4.0 | 4.0 |
|   | Sustention of gloss | 3.5 | 3.7 | 3.8 | 4.0 | 3.9 |
|   | Suppression of oil separation at 50° C. | 4 | 4 | 4 | 4 | 4 |

TABLE 4

|   | Component (mass %) | Example 38 | Example 39 | Comp. 1 | Comp. 2 | Comp. 3 | Comp. 4 | Comp. 5 |
|---|---|---|---|---|---|---|---|---|
| A | Myristic acid | | | | | | | |
|   | Stearic acid | 3.5 | 2.0 | | 5.0 | 5.0 | 5.0 | 0.3 |
|   | Behenic acid | | 1.8 | | | | | |
| B | L-arginine | 0.35 | 0.35 | 0.50 | | 2.50 | 0.80 | 0.05 |
|   | 2-Amino-2-methyl-1-propanol | | | | | | | |
|   | Triethanolamine | | | | | | | |
| C | Sodium hydroxide | 0.40 | 0.40 | 0.40 | 0.60 | | 0.40 | 0.05 |
|   | Potassium hydroxide | | | | | | | |
| D | Myristyl alcohol | | | | | | | |
|   | Stearyl alcohol | | | | | | | |
|   | Cetostearyl alcohol | 3.0 | 3.0 | 6.0 | 6.0 | 6.0 | | 0.4 |
|   | Behenyl alcohol | | | | | | | |
| E | Alkyl benzoate (C12-C15) | 5.0 | 5.0 | 5.0 | 5.0 | 5.0 | 5.0 | 0.1 |
|   | Isopropyl palmitate | | | | | | | |
|   | Mineral oil | | | | | | | |
|   | Silicone oil (200 cs) | | | | | | | |
|   | Triethylhexanoin | | | | | | | |
| F | Water | Balance | Balance | Balance | Balance | Balance | Balance | Balance |
| G | Ceteareth-20 (HLB 12.0) | 0.5 | 0.5 | | | | | |
|   | Laureth-3 (HLB 7.0) | 0.5 | 0.5 | | | | | |
|   | Glycerin monostearic acid ester (HLB3.4) | | | | | | | |
|   | PEG-30 hydrogenated castor oil (HLB 11.0) | | | | | | | |
| H | Sodium lauryl ether phosphate (SPE-104NB) | | 0.3 | | | | | |
|   | Sodium stearoyl methyltaurine (NIKKOL SMT) | | | | | | | |
|   | Sodium N-stearoyl-L-glutamate (AMISOFT HS-11P) | 0.5 | | | | | | |
|   | Total | 100.0 | 100.0 | 100.0 | 100.0 | 100.0 | 100.0 | 100.0 |
|   | A + D | 6.5 | 6.8 | 6.0 | 11.0 | 11.0 | 5.0 | 0.7 |
|   | A/(A + D) Mass ratio | 0.54 | 0.56 | — | 0.45 | 0.45 | 1.00 | 0.43 |
|   | B/(B + C) Molar ratio (mol %) | 16.7 | 16.7 | 22.3 | — | 100.0 | 31.4 | 18.6 |
|   | (B + C)/A Molar ratio (mol %) | 97.6 | 97.5 | — | 85.4 | 81.7 | 83.0 | 145.8 |
|   | (A + D)/G Mass ratio | 6.5 | 6.8 | — | — | — | — | — |
|   | E/(A + D) Mass ratio | 0.77 | 0.74 | 0.83 | 0.45 | 0.45 | 1.00 | 0.14 |
|   | H/(G + H) Mass ratio | 0.00 | 0.23 | — | — | — | — | — |
|   | Concentric lamella (preparation) | Y | Y | N | Y | N | N | N |
|   | Concentric lamella (coating film) | Y | Y | N | Y | N | N | N |
|   | Moisturizing properties (moisture-confining properties) | 60 | 65 | 6 | 23 | 30 | 11 | 10 |
|   | Oily feel | 3.8 | 3.9 | 1.2 | 2.0 | 1.7 | 1.5 | 2.8 |
|   | Sustention of softness of skin | 3.8 | 4.0 | 1.3 | 1.4 | 2.0 | 1.4 | 1.6 |
|   | Sustention of gloss | 3.9 | 4.0 | 1.1 | 1.8 | 1.7 | 1.4 | 1.3 |
|   | Suppression of oil separation at 50° C. | 4 | 4 | 1 | 1 | 2 | 1 | 1 |

|   | Component (mass %) | Comp. 6 | Comp. 7 | Comp. 8 | Comp. 9 | Comp. 10 |
|---|---|---|---|---|---|---|
| A | Myristic acid | | | | | |
|   | Stearic acid | 9.0 | 5.0 | 5.0 | 3.5 | 2 |
|   | Behenic acid | | | | | |
| B | L-arginine | 2.00 | 0.05 | 0.70 | 0.50 | 0.45 |
|   | 2-Amino-2-methyl-1-propanol | | | | | |
|   | Triethanolamine | | | | | |
| C | Sodium hydroxide | 1.00 | 0.05 | 1.00 | 0.40 | 0.13 |
|   | Potassium hydroxide | | | | | |
| D | Myristyl alcohol | | | | | |
|   | Stearyl alcohol | | | | | |
|   | Cetostearyl alcohol | 10.0 | 6.0 | 6.0 | 4.0 | 0.5 |
|   | Behenyl alcohol | | | | | |
| E | Alkyl benzoate (C12-C15) | 10.0 | 5.0 | 5.0 | 25.0 | 1.5 |
|   | Isopropyl palmitate | | | | | |
|   | Mineral oil | | | | | |
|   | Silicone oil (200 cs) | | | | | |
|   | Triethylhexanoin | | | | | |
| F | Water | Balance | Balance | Balance | Balance | Balance |
| G | Ceteareth-20 (HLB 12.0) | | | | | |
|   | Laureth-3 (HLB 7.0) | | | | | |
|   | Glycerin monostearic acid ester (HLB3.4) | | | | | |
|   | PEG-30 hydrogenated castor oil (HLB 11.0) | | | | | |
| H | Sodium lauryl ether phosphate (SPE-104NB) | | | | | |
|   | Sodium stearoyl methyltaurine (NIKKOL SMT) | | | | | |
|   | Sodium N-stearoyl-L-glutamate (AMISOFT HS-11P) | | | | | |
|   | Total | 100.0 | 100.0 | 100.0 | 100.0 | 100.0 |
|   | A + D | 19.0 | 11.0 | 11.0 | 7.5 | 2.5 |
|   | A/(A + D) Mass ratio | 0.47 | 0.45 | 0.45 | — | 0.80 |
|   | B/(B + C) Molar ratio (mol %) | 31.4 | 18.6 | 13.8 | 22.3 | 44.2 |

TABLE 4-continued

| | | | | | |
|---|---|---|---|---|---|
| (B + C)/A Molar ratio (mol %) | 115.3 | 8.7 | 165.1 | — | 83.0 |
| (A + D)/G Mass ratio | — | — | — | — | — |
| E/(A + D) Mass ratio | 0.53 | 0.45 | 0.45 | 3.33 | 0.60 |
| H/(G + H) Mass ratio | — | — | — | — | — |
| Concentric lamella (preparation) | Y | N | Y | N | Y |
| Concentric lamella (coating film) | Y | N | Y | N | Y |
| Moisturizing properties (moisture-confining properties) | 30 | 19 | 20 | 6 | 33 |
| Oily feel | 1.4 | 1.3 | 1.8 | 1.5 | 2.0 |
| Sustention of softness of skin | 1.1 | 1.4 | 1.2 | 1.4 | 1.9 |
| Sustention of gloss | 1.2 | 1.5 | 1.9 | 1.7 | 1.9 |
| Suppression of oil separation at 50° C. | 2 | 1 | 2 | 1 | 2 |

The invention claimed is:

1. A skin cosmetic comprising the following components (A), (B), (C), (D), (E), and (F):
   (A) 0.5 to 7 mass % of a linear saturated fatty acid having 12 to 22 of carbon atom,
   (B) 0.01 to 5 mass % of an organic base,
   (C) 0.01 to 1 mass % of an inorganic base,
   (D) 0.6 to 7 mass % of a linear saturated alcohol having 12 to 22 of carbon atom,
   (E) 0.1 to 20 mass % of an oil agent, and
   (F) water,
   wherein
   the total amount of the components (A) and (D) is (A)+(D)=from 1 to 14 mass %, the mass ratio of the component (A) to the total amount of the components (A) and (D) [(A)+(D)] is (A)/[(A)+(D)]=from 0.1 to 0.9, the molar ratio of the component (B) to the total amount of the components (B) and (C) [(B)+(C)] is (B)/[(B)+(C)]=from 5 to 50 mol %, and the molar ratio of the total amount of the components (B) and (C) [(B)+(C)] to the component (A) is [(B)+(C)]/(A)=more than 80 mol % and 120 mol % or less.

2. The skin cosmetic according to claim 1, wherein the component (E) is an oil agent having an SP value of from 16.0 to 21.0.

3. The skin cosmetic according to claim 1, wherein the mass ratio of the component (E) to the total amount of the components (A) and (D) [(A)+(D)] is (E)/[(A)+(D)]=from 0.1 to 3.

4. The skin cosmetic according to claim 1, further comprising 0.1 to 2 mass % of (G) a nonionic surfactant.

5. The skin cosmetic according to claim 4, wherein the mass ratio of the total amount of the components (A) and (D) [(A)+(D)] to the component (G) is [(A)+(D)]/(G)=from 3 to 30.

6. The skin cosmetic according to claim 1, further comprising 0.01 to 1 mass % of (H) an ionic surfactant.

7. The skin cosmetic according to claim 6, wherein the mass ratio of the component (H) to the total amount of the components (G) and (H) [(G)+(H)] is (H)/[(G)+(H)]=from 0.01 to 0.75.

8. The skin cosmetic according to claim 1, wherein the component (B) is at least one member selected from the group consisting of an alkylamine having an alkyl group having 1 to 6 of carbon atom, an alkanolamine having an alkyl group having 1 to 6 of carbon atom, and a basic amino acid.

9. The skin cosmetic according to claim 1, wherein the component (C) is an alkali hydroxide.

* * * * *